United States Patent [19]

Klein

[11] Patent Number: 4,660,560

[45] Date of Patent: Apr. 28, 1987

[54] METHOD FOR TREATING OBSTRUCTIVE PROSTATISM

[75] Inventor: Lester A. Klein, Boston, Mass.

[73] Assignee: The Beth Israel Hospital Association, Boston, Mass.

[21] Appl. No.: 739,128

[22] Filed: May 30, 1985

[51] Int. Cl.$^4$ .......................................... A61M 29/02
[52] U.S. Cl. ..................................... 128/344; 604/101
[58] Field of Search .................. 128/344, 325; 604/96, 604/101, 102, 54

[56] References Cited

U.S. PATENT DOCUMENTS

| | | |
|---|---|---|
| 550,238 | 11/1895 | Allen, Jr. |
| 2,078,686 | 4/1937 | Rowe |
| 2,642,874 | 6/1953 | Keeling |
| 2,849,002 | 8/1958 | Oddo ................................. 604/101 |
| 2,936,760 | 5/1960 | Gants |
| 3,977,408 | 8/1976 | MacKew |
| 4,141,364 | 2/1979 | Schultze |
| 4,205,691 | 6/1980 | Patel |
| 4,219,026 | 8/1980 | Layton |
| 4,311,146 | 1/1982 | Wonder |
| 4,432,757 | 2/1984 | Davis, Jr. |

Primary Examiner—Carroll B. Dority, Jr.
Attorney, Agent, or Firm—Pahl, Lorusso & Loud

[57] ABSTRACT

The present invention is a method for treating obstructive prostatism in which a urethral catheter having a remotely fixed annular balloon is inserted into the urethra and urged therethrough until it is adjacent to the prostate gland. The annular balloon is inflated until the prostate has been forced back from around the urethra. A distally fixed Foley-type balloon may additionally be used to position the annular balloon with respect to the prostate. In the preferred embodiment, the distance between the bladder neck and the bottom of the prostate gland is first determined in order that the attending physician may use an annular balloon of the appropriate length, so as to optimize the effectiveness of the treatment. In order to measure this distance, a calibrated catheter is inserted through the urethra up into the bladder and then anchored at one end to the bladder neck by means of a balloon located at the distal end. A cystoscope may be used to read the markings on the calibrated catheter relative to the prostatic urethra, thereby providing an accurate means for determining the length of the annular balloon to be inserted for dilation. The length of the annular dilating balloon chosen is determined by the length of the prostate gland as measured from the calibrations. The cystoscope may also be used as the means by which both the calibrating catheter and the dilating annular balloon are inserted into the urethra. Multichannel or multi lumen cystoscopes are available for use in this process.

9 Claims, 3 Drawing Figures

METHOD FOR TREATING OBSTRUCTIVE PROSTATISM

BACKGROUND OF THE INVENTION

Obstruction of the urinary tract due to compression of the urethra by an enlarging prostate gland results in a number of symptoms in the patient, including nocturia, frequency of urination, stranguria and post-void dribbling, as well as the emotional problems of pain, discomfort and embarrasment. Generally, patients suffering from such symptomatic prostatism may pursue only two options; either, continue living with the pain and discomfort, or undertake major surgery known as prostatectomy Choosing the surgical procedure subjects the patient to a number of hazards, including post-operative bleeding, stricture formation at the urethra or bladder neck, incontinence, post-manipulation pain or bladder spasm, urinary infection, reactive urethral swelling causing urinary obstruction and epididymitis. Further risks include wound infection, retention of prostatic chips, retrograde ejaculation, bladder perforation, hyponatremia, intravascular hemolysis, and impotency. Moreover, simple prostatectomy requires at least 1 to 3 hours in the operating room, followed by an average of one week in the hospital and in complicated cases, two or more weeks. About 10 to 15% of prostatectomy patients ultimately require a repeat prostatectomy and probably 10% develop strictures with long term cost considerations. Conversely, choosing to abstain from surgery neither alleviates the patient's pain or discomfort nor reduces the probability that more serious future prostate problems will occur.

A number of methods have been used to try and treat prostatism other than with surgery. Such methods frequently utilize the injection of medications into the prostate gland by means of a catheter. These injections are frequently ineffective due both to the poor absorption of antibiotics by the prostate gland, as well as to the difficulty inherent in positioning and retaining the catheter with respect to the affected area, and generally result in reoccuring prostatic disorders following a short period of time. Alternatively, U.S. Pat. Nos. 3,977,408; 2,642,874; and 550,238 teach that distally fixed balloons have been implemented to hold catheters in place while medication is applied to the prostate gland. Balloons located along two sections of a catheter have been used to isolate an area within the urethra, as taught in Gants, U.S. Pat. No. 2,936,760 and Allen, U.S. Pat. No. 550,238.

While balloon catheters have also been used to expand the bladder in order to measure the pressure within the bladder, as expounded in U.S. Pat. Nos. 3,977,391; 4,407,301; 4,191,196 and 4,072,144. Utilizing catheters to seal off an area of the urethra prior to injecting a liquid has been suggested by Rowe, U.S. Pat. No. 2,078,686 and Keeling, U.S. Pat. No. 3,977,408. And, finally, a balloon catheter has also been used to apply pressure following surgery in order to stop bleeding. Examples of such a use are taught in Layton, U.S. Pat. No. 4,219,026 and in Schulze, U.S. Pat. No. 4,141,364. Notwithstanding this concentration of balloon associated catheters, it is certainly clear that none of the prior articles suggest nor anticipate utilizing the balloon itself to dilate the prostatic urethra, as in the present invention. Rather, the prior art teaches only a mechanical stabilizing use subservient to the present invention's intended function of treating an enlarged prostate gland; for which none of these methods have been effective.

SUMMARY OF THE INVENTION

The present invention is a method for treating obstructive prostatism. The present invention is based on the discovery that obstructive prostatism can be treated by exerting pressure through the urethra against the prostate gland. Such pressure forces the prostate gland into an anatomical position from which it no longer restricts the urethra. In one important embodiment of the invention a urethral dilating catheter having a remotely fixed annular balloon is inserted through the urethra until it is adjacent to the prostatic gland as defined at its top by the bladder neck and its bottom by the verumontanum. At this point the annular balloon is expanded, forcing the prostate gland away from the urethra and, therefore, eliminating the urethral obstruction. Once the dilating catheter is withdrawn from the urethra, the prostate gland no longer obstructs the urethra.

In the preferred embodiment, a multichannel cystoscope is inserted through the urethra up into the bladder. A calibrated catheter is inserted through a lumen in the cystoscope and urged upwards until it reaches the bladder. A Foley-type balloon located on the distal end of the calibrated catheter is expanded. The calibrated catheter is then slightly withdrawn in order to anchor the balloon catheter to the neck of the bladder. The cystoscope is then withdrawn until the optical piece is located immediately below the prostate gland. The calibration marks on the calibrated catheter are then visually discernable and the length between the neck of the bladder and the veru montanum is easily measured. The balloon on the calibrating catheter is then deflated and the calibrated catheter is withdrawn. A second catheter (a dilating catheter), also having a balloon at the distal end, and further having a remotely fixed annular balloon extending from the distal end for a length equivalent to the length of the just measured prostate gland, is inserted through the urethra until the balloon at the distal end is located within the bladder. The distal balloon is then inflated and the catheter withdrawn until it engages the bladder neck, fixedly positioning the annular balloon with respect to the prostatic gland. The annular balloon located along the length of the affected prostate gland is then inflated, and the prostate is forced away from the urethral lumen.

The dilating balloon may be left in place for periods of up to an hour or more in order to optimize the dilation effect upon the urethra. Subsequent to reaching the desired urethral dilation, both the anchoring balloon and the expanded remote annular balloon are deflated and the catheter is withdrawn.

Accordingly, it is the primary object of the present invention to provide a new non-surgical method for pressure dilating the prostate in order to relieve the symptoms of obstructive prostatism.

It is another object of the present invention to provide a method for treating prostatic disorders which affords patients the opportunity to elect an additional option of treatment distinct from choosing either simply continuing to live with the pain and discomfort or, conversely, undertaking prostatectomy with its attendant risks.

It is another object of this invention to provide a method that is simple to perform, relatively inexpensive, and which is accompanied by little risk to the patient.

It is another object of this invention that this method be readily adaptable to each patient's particular prostatic disorder.

It is a still further object of the present invention to provide a method which can be performed as an outpatient procedure not requiring general anesthesia.

BRIEF DESCRIPTION OF THE DRAWING

These and other details and advantages of the invention will be described in connection with the accompanying drawing, in which.

DESCRIPTION OF THE PREFERRED EMBODIMENT

Figure 1:
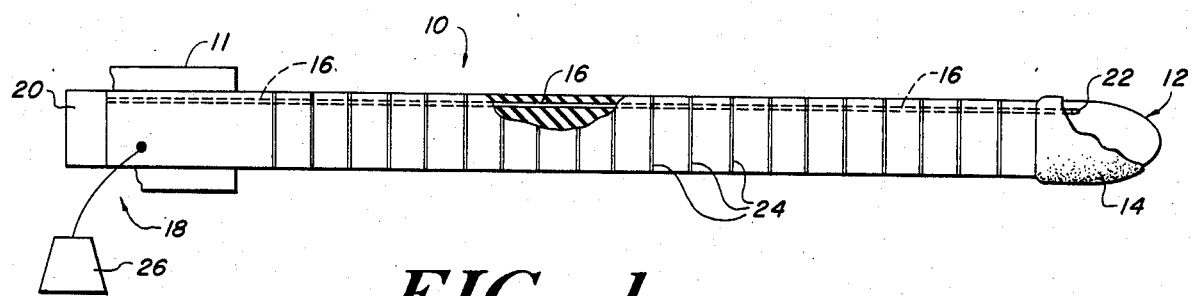
FIG. 1 is a perspective view, in partial section, of the calibrated catheter utilized to measure the length of the prostatic gland when performing the preferred embodiment of the invention.

The preferred embodiment of the present invention utilizes a calibrated catheter 10 as shown in FIG. 1 which is received through a lumen in multichannel cystoscope 11, and includes a distal end 12 upon which a Foley-type balloon 14 is fixed. Conduit 16 extends through and along the length of the calibrated catheter from the distal end 12 to a proximal end 18 where it terminates into a dual valve 20 in communication with a liquid cystokon supply not shown. Activating dual valve 20 initiates fluid flow which travels from the proximal end 18 to the distal end 12 of calibrated catheter 10, and then progresses down the path of least resistance through hole 22 communicating with the interior of Foley-balloon 14 which expands relative to the fluid velocity and volume. In an alternative embodiment types of fluid or gas may be used to inflate the Foley-balloon. Such procedures are, of course, known to those skilled in this art. Calibration marks 24 extending along the exterior face of catheter 10 are read from distal end 12 to proximal end 18 since it is distal end 12 which will be fixedly positioned adjacent to the bladder neck, enabling measurement of the prostatic gland length. The distance separating each calibrating indicia 24 is dependent upon the measurement system selected, with quarter of an inch increments being used in the preferred embodiment.

Figure 2:
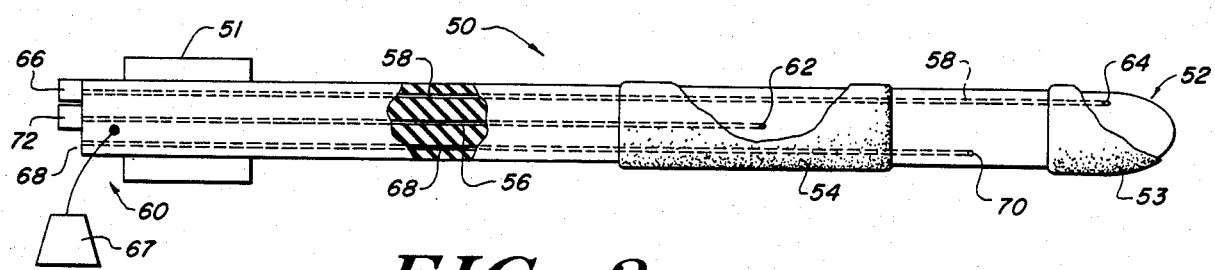
FIG. 2 is a perspective view, partly in section, of the urethral dilating catheter used to dilate the prostatic urethra in accordance with the present invention; and, FIG. 3 is a cross-sectional view of the urethral dilating catheter as applied to the male urinary tract.

The operation of the calibrated catheter 10 commences with distal end 12 insertion into the penile meatus through the urethra and into the bladder. Depending upon the patient's sensitivity and his extent of prostatic pain, local anesthesia may be required at this time. Subsequent to distal end 12 entering the bladder, valve 20 is activated enabling conduit 16 to communicate with the liquid cystokon supply thereby inflating the Foley-balloon 14 inside the bladder. Closing valve 20 halts the flow of liquid cystokon both to and from the Foley-balloon 14, remotely sealing the inflated balloon within the bladder. Calibrated catheter 10 is slowly withdrawn until Foley-balloon 14 lodges into the bladder neck, fixedly positioning the initial calibration mark with respect to the bladder neck. A simple weight 26 or other means of tensing the catheter may be removably fixed to proximal end 18 in order to securely maintain engagement of the anchoring balloon 14 to the bladder neck. Withdrawing multichannel cystoscope 12 until its lens is positioned directly below the prostate facilitates reading the calibrating indicia 24. Summating the number of calibrations 24 extending between the bladder neck and veru montanum will result in a measurement corresponding to the length of the affected prostatic urethra and will additionally serve as the length selected for the remotely fixed annular dilating balloon 54 (FIG. 2). Releasing the liquid cystokon through valve 20 deflates Foley-balloon 14, enabling removal of calibrated catheter 10 once an accurate and satisfactory measurement of the length of the prostate gland has been made.

The dilating catheter assembly 50 of FIG. 2 utilized to pressure dilate the prostatic urethra is inserted through a multichannel cystoscope 51 lumen and includes a distal end 52 upon which a Foley-balloon 53 is fixed, and an annular balloon 54 disposed proximate to the distal end 52. A pair of parallel conduits 56 and 58 extend from proximal end 60, with conduit 56 terminating in hole 62 which is in communication with the annular balloon 54 interior, and conduit 58 terminating in hole 64 which communicates with the Foley-balloon 53 interior. Annular balloon 54 length along the catheter is equivalent to that measurement garnered from using the calibrated catheter and in the preferred embodiment a plurality of dilating catheter assemblies of varying length are kept on hand so that regardless of the size of the prostatic urethra being treated, a catheter assembly with equivalently long annular balloon will be prepared for insertion.

In the preferred embodiment distal end 52 is received through a lumen in cystoscope 51 and urged through the urethra into the bladder. It may be taken for granted that such a procedure is most likely preceded by application of analgesia. Valve 66, communicating with the liquid cystokon supply and conduit 58, is slowly opened thereby inflating the Foley-balloon 53 now within the bladder. Closing valve 66 remotely seals the balloon 53, and a slight withdrawal of the catheter assembly 50 engages the expanded balloon 53 to the bladder neck, fixedly positioning annular balloon 54 with respect to the prostatic gland as defined by the bladder neck and veru montanum. Again, a weight 67 may be removably fixed to the proximal end 60 in order to maintain the anchoring of the Foley-balloon 53 to the bladder neck. At this time, medication facilitating dilation of the urethra, such as xycocaine, may be injected into conduit 68 and applied to the prostatic urethra through aperture 70 disposed directly above annular balloon 54. Valve 72 is now opened slightly in order to regulate slowly the liquid cystokon flow and the expansion of annular balloon 54 resulting therefrom. Subsequent to reaching the desired expansion, valve 72 is closed, remotely sealing annular balloon 54 and retaining it in a dilating position within and against the urethra. Depending upon the gravity of the prostate encroachment and the disorder related thereto, annular balloon 54 may be left untouched for periods up to an hour or more so as to optimize the dilating affect. Subsequent to attaining sufficient pressure dilation of the urethra, both two way valves 66 and 72 may be activated to release the liquid cystokon, thereby deflating both Foley-balloon 53 and annular balloon 54 and enabling withdrawal of the dilating catheter assembly 50.

Figure 3:
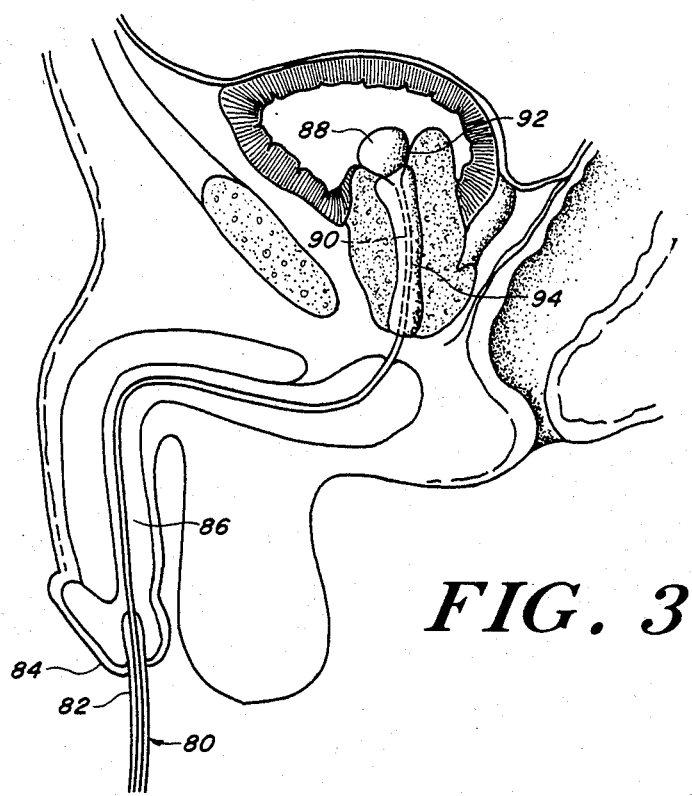

FIG. 3 illustrates a cross-sectional view of dilating catheter assembly 80 as utilized within the male urinary tract in accordance with the present invention. Multichannel cystoscope 82 is received through penile meatus 84 and lodges in the urethra 86 where it receives dilating catheter 80 through one of its lumens. Expanded Foley-balloon 88 is anchored to the bladder neck 92 while annular balloon 90 is fixedly positioned with respect to the prostatic urethra as defined by the bladder neck 92 and the veru montanum 94. Pressure dilation of the prostatic urethra by annular balloon 90 continues as long as it is deemed necessary. In the preferred embodiment, X-ray examination is performed in order to ensure that each component is in its correct location and proper orientation.

It is understood that the preceding description is given merely by way of illustration and not in limitation of the invention and that various modifications may be made thereto without departing from the spirit of the invention as claimed.

I claim:

1. A method of dilating a prostatic urethra, which comprises:
   introducing a multichannel cystoscope into and along the length of the prostatic urethra;
   passing a urethral catheter through a lumen in the cystoscope into the prostatic urethra and along thereto;
   positioning a remote section of the urethral catheter between and adjacent to the bladder neck and the veru montanum; and,
   expanding the remote section annularly in order to dilate the prostatic urethra and thereby relieve the prostatic encroachment thereto.

2. A method as recited in claim 1 wherein said positioning step comprises anchoring the distal end of the urethral catheter to the bladder neck, thereby positioning the remote section with respect to the prostatic urethra as defined by the bladder neck and the veru montanum.

3. A method as recited in claim 2 wherein said anchoring step comprises:
   expanding a balloon fixed to the distal end of the urethral catheter subsequent to its passing through the urethra and into the bladder; and,
   engaging the expanded balloon to the bladder neck.

4. A method of dilating a prostatic urethra, which comprises:
   measuring the distance between the bladder neck and the veru montanum;
   inserting a dilating catheter into the urethra and along therethrough, wherein the dilating catheter has an expandable remote section of a length equivalent to that of the measured distance;
   positioning the remote section of the dilating catheter between and adjacent to the bladder neck and the veru montanum; and,
   expanding said remote section annularly in order to dilate the prostatic urethra and thereby relieve the prostatic encroachment thereto.

5. A method as recited in claim 4 wherein said measuring step comprises:
   introducing a multichannel cystoscope into and along the urethra;
   passing a calibrated catheter through a lumen in the cystoscope until the distal end progresses to the bladder neck;
   discerning the number of calibrations extending along the calibrated catheter between the veru montanum and the bladder neck; and,
   withdrawing the calibrated catheter.

6. A method as recited in claim 5 wherein said passing step further comprises the step of anchoring a distal end of the calibrated catheter to the bladder neck, thereby securely fixing the catheter in a position enabling of accurate reading of the quantity of calibrations between the bladder neck and the veru montanum.

7. A method as recited in claim 6 wherein said anchoring step comprises:
   expanding a balloon fixed to the distal end of the calibrated catheter subsequent to its passing through the urethra and into the bladder; and,
   engaging the expanded balloon to the walls of the bladder neck.

8. A method as recited in claim 4 wherein said positioning step comprises:
   anchoring the distal end of the dilating catheter to the bladder neck, thereby fixedly positioning the remote section with respect to the prostatic urethra as defined by the bladder neck and the veru montanum.

9. A method as recited in claim 8 wherein said anchoring step comprises:
   expanding a balloon fixed to the distal end of the dilating catheter subsequent to its passing through the urethra and into the bladder; and,
   engaging the expanded balloon to the bladder neck.

* * * * *